US005941839A

United States Patent [19]

Ishikawa

[11] Patent Number: 5,941,839

[45] Date of Patent: Aug. 24, 1999

[54] ROTARY APPARATUS

[75] Inventor: Kiyoshi Ishikawa, Ako, Japan

[73] Assignee: Akiko Ishikawa, Nakahirokita, Japan

[21] Appl. No.: 08/941,329

[22] Filed: Sep. 30, 1997

[51] Int. Cl.[6] .................................................. A61M 1/00

[52] U.S. Cl. ............................... 601/23; 601/24; 601/26; 128/200.24; 128/202.11; 128/204.18; 128/202.13

[58] Field of Search .................................. 601/5, 23, 24, 601/26, 41, 84–86, 89, 90, 97, 98, 112, 115; 482/13, 30, 51, 77, 110, 142, 146, 147; 472/14, 25, 26, 130; 434/55, 59, 258, 260, 261; 128/200.24, 201.19, 201.29, 202.11, 202.13, 202.16, 202.27, 204.18, 204.29, 205.11; 297/180.16

[56] References Cited

U.S. PATENT DOCUMENTS

| | | | |
|---|---|---|---|
| 957,739 | 5/1910 | Bules | 297/180.16 |
| 1,118,353 | 11/1914 | Jurkowski | 297/180.16 |
| 3,176,687 | 4/1965 | Barach | 128/202.13 |
| 4,045,044 | 8/1977 | Bierer | 128/202.13 |
| 5,477,850 | 12/1995 | Zegler et al. | 128/202.11 |
| 5,562,091 | 10/1996 | Foster | 128/200.24 |
| 5,622,503 | 4/1997 | Feng | 434/59 |

FOREIGN PATENT DOCUMENTS

| | | | |
|---|---|---|---|
| 5-42176 | 2/1993 | Japan | 601/24 |

OTHER PUBLICATIONS

Alvan L. Barach, M.D., "Pulmonary Emphysema" May 1966.

*Primary Examiner*—Jeanne M. Clark
*Attorney, Agent, or Firm*—Marshall, O'Toole, Gerstein, Murray & Borun

[57] ABSTRACT

A rotary apparatus gives a patient a rotational motion at a discretionary controlled speed suitable to medical treatment and at the same time can continuously supply the patient in rotation with oxygen for inhalation by means of oxygen supply equipment. The apparatus is characterized in that a chair 1 on which a patient is sitting is driven, via a rotary shaft 6, by a driving system 3 installed in a control base 2 to rotate, and oxygen for inhalation to be supplied to the patient in rotation is guided to pass through the interior of the rotary shaft 6 and supplied by a mouthpiece 23 provided at the top end of an oxygen supply tube 21 to a position suitable for the patient to breathe.

2 Claims, 3 Drawing Sheets

ROTARY APPARATUS

The present invention relates to a rotary apparatus that gives a rotational motion to a patient who needs medical treatment at a controlled speed and is provided with equipment that can supply oxygen for inhalation to the patient in rotation.

It is a well-known art (U.S. Pat. No. 5,547,460) to place a patient, according to her or his symptoms and signs, on a rotary apparatus and give a rotational motion to the patient at an appropriate speed that is effective in recovering the health of the patient so as to promote curing. The present invention relates to a rotary apparatus with additional equipment arranged to supply oxygen for inhalation to a patient in rotation at a point appropriate for the patient to breathe so as to further enhance the above-mentioned promotional effect.

In the past, of means for supplying oxygen for inhalation to a patient at rest, the most simple and generally practiced method is to attach a funnel-shaped mouthpiece to the top end of a supply pipe connected to an oxygen gas supply source and bring the mouthpiece to a position appropriate for the patient to breathe so that the patient inhales oxygen gas released from the mouthpiece. As one can imagine easily, the net quantity of oxygen that can be inhaled by the patient is several tens percent or several percent of the total quantity of oxygen released from the mouthpiece. The rest is dispersed in the room. It is a very inefficient method.

A method of increasing the oxygen consumption efficiency is the so-called hyperbaric oxygen chamber. A patient is placed in a hyperbaric oxygen chamber, and the chamber is sealed. Then hyperbaric oxygen is fed into the chamber. In this way, waste of oxygen gas is prevented, and the retained pressure of oxygen gas in the chamber can be freely selected to meet the needs of the patient. This contributes to promotion of therapeutic effects.

As explained above, there are various systems in the prior art of oxygen supply equipment. Moreover, it has been practiced to place a patient on a rotary apparatus to give the patient a rotational motion suitable to recover or sustain health. However, a rotary apparatus is not known in the art that can give a rotary motion to a patient at a controlled speed that is appropriate for treatment and at the same time can supply the patient in rotation with oxygen for inhalation continuously by means of oxygen supply equipment. Further, no rotary apparatus has been embodied that can correlate the rotational speed of the rotary apparatus with the oxygen supply rate to adjust the ratio of the two properly and in an automatic manner.

SUMMARY OF THE INVENTION

The present invention was made in view of the present state of the prior art as mentioned above and is intended to realize a rotary apparatus that gives a patient a rotational motion at a desired controlled speed suitable to treatment and at the same time can supply the patient in rotation with oxygen for inhalation continuously by means of oxygen supply equipment.

Another objective of the present invention is to provide a rotary apparatus wherein the oxygen supply equipment is skillfully installed in a space in which the oxygen supply equipment does not disturb the patient in rotation hence the patient under treatment can receive therapy in a comfortable condition.

Another objective of the present invention is to provide a rotary apparatus wherein the adjustment of a desirable relationship between the rotational speed of the rotary apparatus and the oxygen supply rate of the oxygen supply equipment is made in a completely automatic manner hence exact therapeutic effects can be attained by simple operation.

The rotary apparatus of the present invention, being a means for solving the above-mentioned objectives, is a rotary apparatus that gives a patient needing medical treatment and riding on the rotary apparatus a forced rotational movement by means of a power system at a controlled speed suitable to treatment, and said rotary apparatus is provided with oxygen supply equipment to supply oxygen for inhalation at a position convenient for the patient to breathe.

To use the rotary apparatus constructed as mentioned above and give medical treatment to a patient placed on the apparatus, the apparatus is started to give the patient a rotational motion at a controlled speed appropriate to treatment. At the same time, a supply of oxygen for inhalation by the patient in rotation is started. The oxygen releasing end piece of the supply equipment is located at a position convenient for the patient to breathe oxygen. In this way, the patient can freely inhale oxygen supplied by the oxygen supply equipment while being forced to undergo a rotational motion suited to treatment.

The above-mentioned oxygen supply equipment may be constructed in such a way that a part or the entirety of the equipment rotates together with the above-mentioned rotary apparatus.

To construct the oxygen supply equipment as mentioned above, it is effective, for example, to construct a transitional part of the flow channel between the rotary portion and the stationary portion of the oxygen supply route as a rotary joint; the rotary joint is a combination of a sleeve (the rotary portion) and a ring groove (the stationary portion). The sleeve is made to rotate in the ring groove, and holes made in the sleeve are made to be constantly exposed to oxygen supplied to the ring groove over the entire range of rotation of 360 degrees. In this way, a smooth connection of the above-mentioned flow channel is realized. When the flow of oxygen in the oxygen supply equipment is connected with a rotary joint provided in the middle thereof, arrangement of the oxygen supply tube, the terminal piece for oxygen inhalation, etc., all downstream of the rotary joint, can be made quite easily.

It is desirable to construct the oxygen supply route of the above-mentioned oxygen supply equipment, as a route that passes a rotary shaft that serves as the main shaft of the rotary apparatus. When the rotary shaft is included in the above-mentioned supply route, if, for example, it is necessary to supply oxygen according to a certain standard and the rotational speed depends upon a control element, the construction of the rotary shaft can be used to easily specify the relationship between the oxygen flow rate and the rotational speed.

Moreover, it is useful to construct the rotary apparatus in such a way that the supply rate of oxygen being supplied by the above-mentioned oxygen supply equipment to a patient can be automatically adjusted according to the rotational speed of the above-mentioned rotary shaft.

For example, a centrifugal system with weights may be provided on the above-mentioned rotary shaft, and the sleeve on the rotary shaft may be made to move against a spring by the centrifugal forces generated by the weights and control the oxygen-passing area. In this way, the oxygen supply rate can be automatically adjusted according to the rotational speed of the rotary apparatus. With this arrangement, the rotational speed can be set automatically at a specific level required by the patient, and at the same time the oxygen supply rate can be set automatically at a specific level required under that condition; as a result, the rotary apparatus can perform exact work with high reliability.

DETAILED DESCRIPTION OF THE INVENTION

Figure 1:
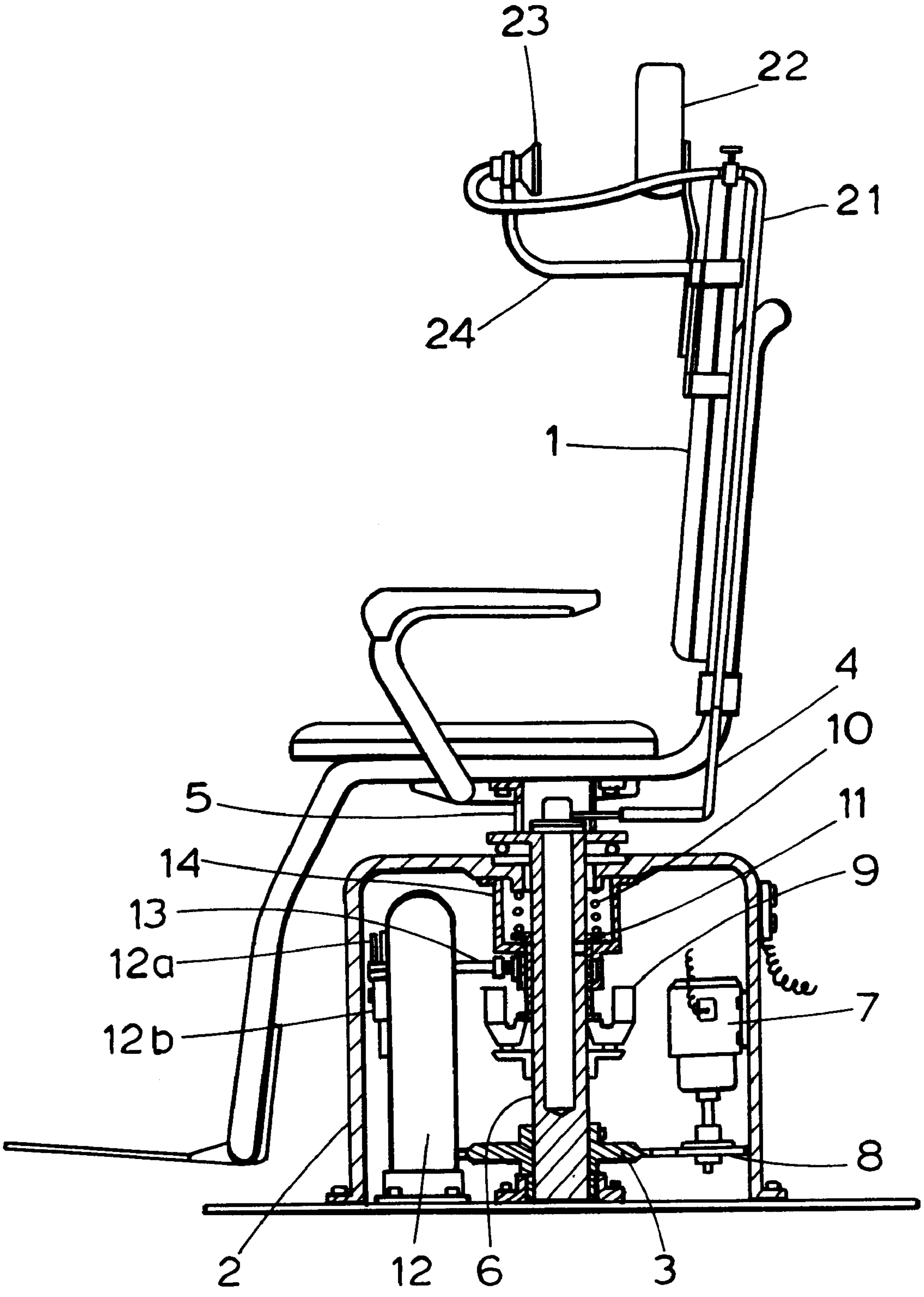
FIG. 1 is a partially sectional side view showing the entirety of an embodiment of the apparatus according to the present invention.
Figure 2:
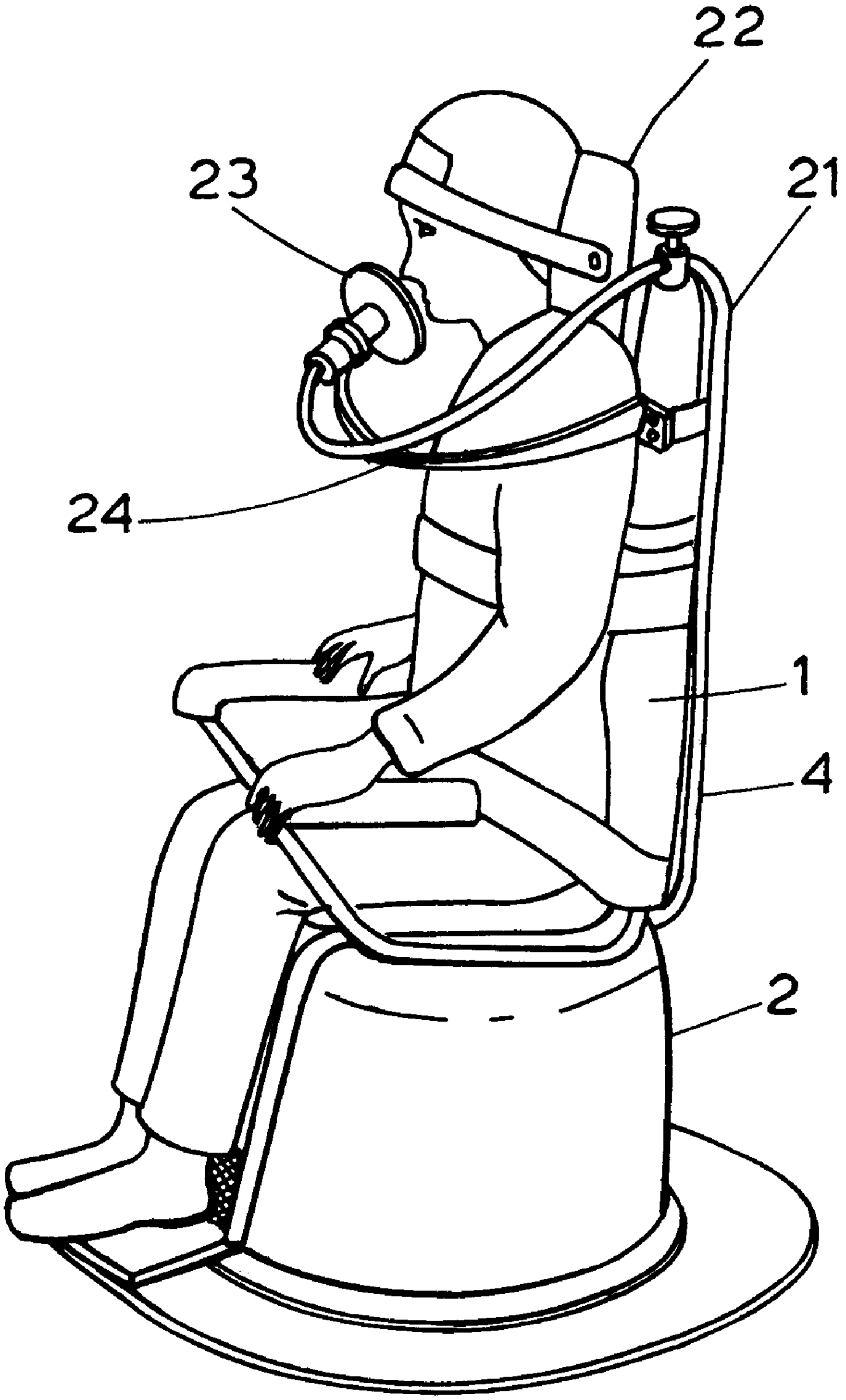
FIG. 2 is a perspective view for describing how the embodiment of FIG. 1 works.
Figure 3:
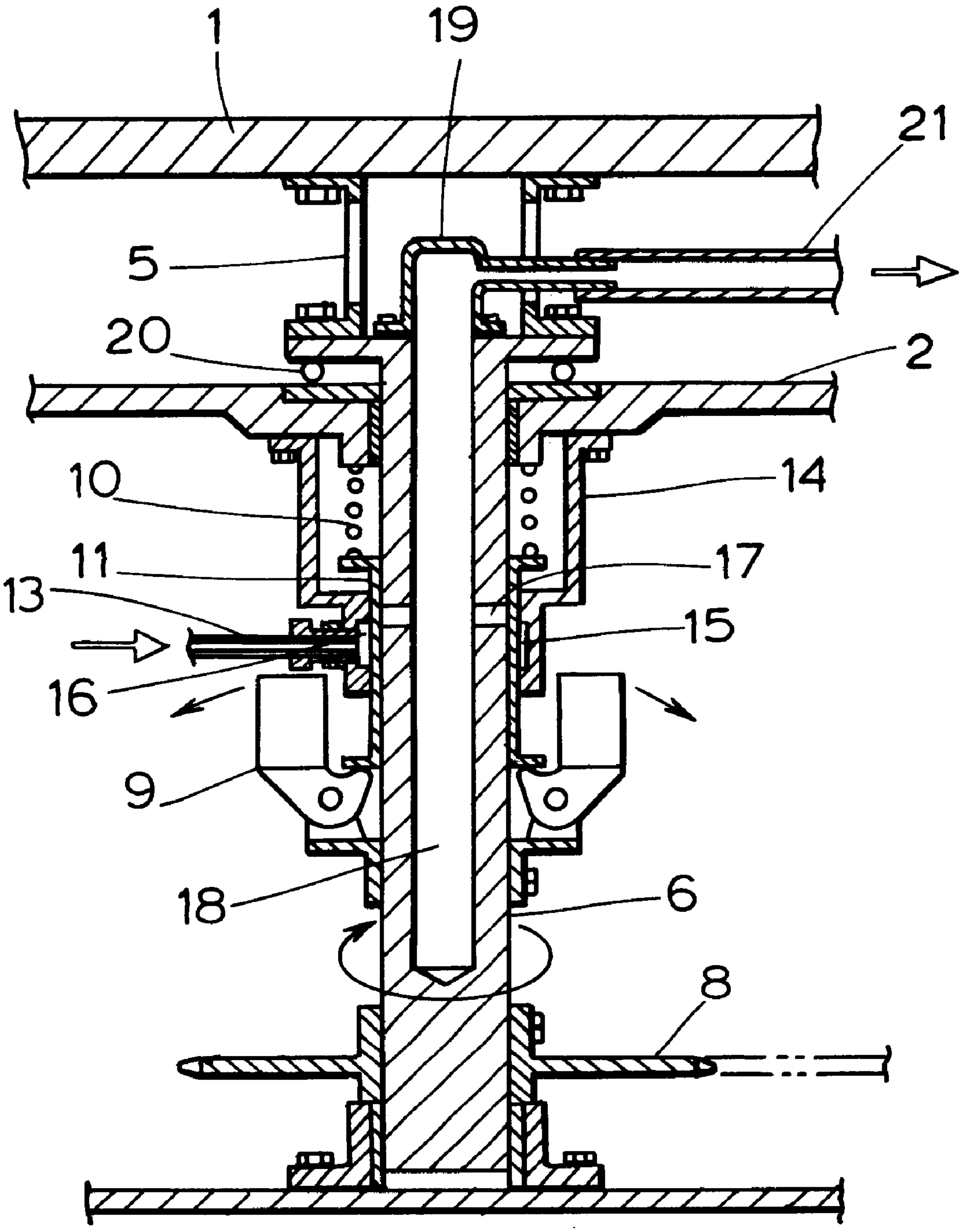
FIG. 3 is a sectional view showing an enlarged relevant part of the embodiment of FIG. 1.

In the following, the forms of the respective embodiments will be described in detail. FIG. 1 is a partially sectional side view of one embodiment, FIG. 2 is a perspective view showing the state of the embodiment in use, and FIG. 3 is an enlarged sectional view of a relevant part of FIG. 1. The rotary apparatus comprises a chair 1 that is structured to be rotatable, a control base 2 that supports the chair 1 above and is structured to be stationary, a driving system 3 that is located in the control base 2 and drives the chair 1 to rotate, and an oxygen supply equipment 4 that is installed between them. A connecting hollow piece 5 is provided between the top of a rotary shaft and the bottom of the chair 1 and drives the chair 1 to rotate according to the rotation of the rotary shaft 6. A motor 7 for driving drives the rotary shaft 6 to rotate via a belt drive mechanism or chain drive mechanism 8.

A system using centrifugal forces of weights is shown as an example of the mechanism for automatically regulating the oxygen supply rate according to the rotational speed of the rotary apparatus. A pair of weights 9, 9 are provided around the rotary shaft 6 in such a way that a sleeve 11 placed over the rotary shaft 6 is pushed upwards against a spring 10 by the centrifugal forces of the weights 9, 9. Oxygen released from an oxygen cylinder 12 is guided through an oxygen flow meter 12*a* and an oxygen humidifier 12*b*, then through an oxygen inlet tube 13 and a sleeve support piece 14 and finally to a ring groove 15 as shown in FIG. 3. 16 denotes sleeve holes bored in the sleeve 11, and 17 denotes a horizontal hole bored in the rotary shaft 6. 18 denotes a central hole made in the rotary shaft along the axial direction thereof. 19 denotes a coupling piece for guiding oxygen from the central hole 18 to the outside of the control base 2, and 20 is a thrust bearing that supports the full weight of the chair 1 and ensures smooth rotational drive of the rotary shaft 6. Oxygen guided by the coupling piece 19 is guided, via an oxygen supply tube 21, to a place near a head rest 22. A mouthpiece 23 is provided at the top end of the oxygen supply tube 21. The mouthpiece 23 is held by a mouthpiece support arm 24, and with this arrangement the mouthpiece 23 can be shifted to a position at which the mouthpiece 23 will not hinder the movement of a patient from or onto the chair 1.

With reference to FIG. 1 through FIG. 3, the effects of the rotary apparatus comprising of the above-mentioned constructions will be described in the following. A patient is guided to sit on the rotary apparatus at rest, and when necessary, the head, the upper body, etc. of the patient are lightly secured to the chair 1 by means of belts (see FIG. 2). Next, the mouthpiece support arm 24 is shifted suitably to bring the mouthpiece 23 to a position convenient for the patient to breathe oxygen. Under that condition, a control panel (not illustrated) that is provided separately is operated to start the motor 7. As a result, the rotary shaft 6 will be driven via the belt drive mechanism or chain drive mechanism 8, and this drive will be transmitted via the connecting hollow piece 5, and the chair 1 will start to rotate.

On the other hand, the above-mentioned control panel is operated to actuate the oxygen supply system. To be more specific, the oxygen cylinder 12 is opened to release oxygen, and this oxygen is put through the oxygen flow meter 12*a* and the oxygen humidifier 12*b*, and then is guided via the oxygen inlet tube 13 into the ring groove 15 provided in the sleeve support piece 14. At this time, the sleeve holes 16 provided in the sleeve 11 are in contact with the ring groove 15, allowing oxygen to flow through. However, passage of oxygen is blocked by the outer circumference of the rotary shaft 6 being in contact with the inner surface of the sleeve 11. This state will be eliminated only when the sleeve 11 moves axially over the rotary shaft 6 and the shaft horizontal hole 17 bored in the rotary shaft 6 is connected through with the sleeve holes 16. Upon the above-mentioned elimination, passage of oxygen is realized, and oxygen in the ring groove 15 will move through the sleeve holes 16 and the shaft horizontal hole 17 and reach the central hole 18 of the rotary shaft 6. Then oxygen moves through the coupling piece 19 and the oxygen supply tube 21 and reaches the mouthpiece 23 to be released towards the patient.

The time when the above-mentioned shaft horizontal hole 17 is continuous with the sleeve holes 16 starts when the rotational speed of the rotary shaft 6 increases gradually and the force pressing upward the lower end of the sleeve 11 due to the centrifugal forces of the weights 9 overcomes the force of the spring 10 to push up the sleeve 11 and the sleeve holes 16 of the sleeve 11 and the shaft horizontal hole 17 of the rotary shaft 6 start to communicate with each other. After that, with the rise in the rotational speed, the sleeve 11 is continued to be pushed up and the sectional flow area generated by the sleeve holes 16 and the shaft horizontal hole 17 overlapping with each other will increase until a certain point is reached. During this period, the rotational speed and the oxygen release rate vary, keeping a fixed correlation with each other that can be preset freely. Hence a rotary apparatus that can accomplish the desired effects can be realized by calculating in advance the rotational speed required by a patient and an oxygen supply rate required in connection with the rotational speed, and properly setting the shapes and sizes of the above-mentioned respective holes so that the desired numerical values of the speed and rate can be attained. It is needless to say that the present invention is applicable to a rotary apparatus that rotates a patient in standing position such as the apparatus of the U.S. Pat. No. 5,547,460 mentioned above, although its illustration is omitted.

As the rotary apparatus of the present invention is constructed as described above, it has the following effects:

1) The apparatus can give a patient a rotational motion suitable to her or his medical treatment, and while maintaining that condition the apparatus can simultaneously and continuously allow the patient to inhale oxygen supplied by the oxygen supply equipment.

2) In some embodiments of the invention in which the oxygen supply equipment is installed skillfully in a space in which the equipment does not disturb the patient, the patient can receive therapy in a comfortable condition all the time.

3) In some embodiments of the invention, the adjustment of the desired relationship between the rotational speed of the rotary apparatus and the oxygen supply rate of the oxygen supply equipment can be made through the rotary shaft and its peripheral components. This contributes to accomplishment of exact results through simple operation.

4) In some embodiments of the invention, the complete regulation of the desired relationship between the rotational speed and the oxygen supply rate is made automatically. This contributes greatly to automation and simplification of the operation of the apparatus.

What is claimed is:

1. A rotary apparatus comprised of:

a base;

a patient platform rotatably mounted to the base;

a shaft connected to the platform for rotating the platform;

an oxygen inlet port;

an oxygen delivery means for delivering oxygen to a patient; and an oxygen supply passage extending from the oxygen inlet means, through the shaft, to the oxygen delivery means.

2. A rotary apparatus of claim 1, further comprising means for automatically correlating the rate of oxygen supply with the speed of rotation of the patient platform.

* * * * *